United States Patent
Penninger et al.

(10) Patent No.: US 12,109,414 B2
(45) Date of Patent: Oct. 8, 2024

(54) BACKGROUND STIMULATION FOR FITTING COCHLEAR IMPLANTS

(71) Applicant: MED-EL Elektromedizinische Geraete GmbH, Innsbruck (AT)

(72) Inventors: Richard Penninger, Innsbruck (AT); Sascha Fuchs, Innsbruck (AT)

(73) Assignee: MED-EL ELEKTROMEDIZINISCHE GERAETE GMBH, Innsbruck (AT)

( * ) Notice: Subject to any disclaimer, the term of this patent is extended or adjusted under 35 U.S.C. 154(b) by 25 days.

(21) Appl. No.: 18/185,913

(22) Filed: Mar. 17, 2023

(65) Prior Publication Data
US 2023/0226353 A1    Jul. 20, 2023

Related U.S. Application Data (63) Continuation of application No. 17/262,662, filed as application No. PCT/US2019/038875 on Jun. 25, 2019, now abandoned.
(Continued)

(51) Int. Cl.
*A61N 1/36* (2006.01)
*A61N 1/05* (2006.01)

(52) U.S. Cl.
CPC ....... *A61N 1/36039* (2017.08); *A61N 1/0541* (2013.01)

(58) Field of Classification Search
CPC .......................... A61N 1/36039; A61N 1/0541
See application file for complete search history.

(56) References Cited

U.S. PATENT DOCUMENTS

| 2006/0235332 A1 | 10/2006 | Smoorenburg |
| 2011/0060384 A1 | 3/2011 | Lineaweaver |
| 2013/0138180 A1 | 5/2013 | Kals et al. |

FOREIGN PATENT DOCUMENTS

| WO | 2012/162349 A1 | 11/2012 |
| WO | 2013/152077 A1 | 10/2013 |

(Continued)

OTHER PUBLICATIONS

International Searching Authority/US, International Search Report and Written Opinion of the International Searching Authority, Application No. PCT/US2019/038875, mailed Sep. 16, 2019, 12 pages.

(Continued)

*Primary Examiner* — Joseph M Dietrich
(74) *Attorney, Agent, or Firm* — BURNS & LEVINSON LLP (57) ABSTRACT

A fitting arrangement is described for fitting electrode contacts of cochlear implant electrode array implanted in a cochlea of an implanted patient. This involves iteratively fitting multiple fitting electrode contacts by for each of the fitting electrode contacts: i. delivering fitting stimulation signals to the fitting electrode contact and at least one neighboring electrode contact to stimulate adjacent auditory neural tissue, wherein the fitting stimulation signals are characterized by a charge level distribution function having a non-zero noise level charge at the at least one neighboring electrode contact and a response level charge much greater than the noise level charge at the fitting electrode contact, and ii. obtaining patient responses from the implanted patient to the fitting stimulation signals. A patient-specific fit map is then defined for the electrode contacts of cochlear implant electrode array based on the patient responses.

8 Claims, 7 Drawing Sheets

Related U.S. Application Data (60) Provisional application No. 62/702,944, filed on Jul. 25, 2018.

(56) References Cited

FOREIGN PATENT DOCUMENTS

| WO | 2018/005583 A1 | 1/2018 |
| WO | 2018/160450 A1 | 9/2018 |

OTHER PUBLICATIONS

European Patent Office, Extended European Search Report, Application No. 19841713.1, dated Mar. 25, 2022, 8 pages.

BACKGROUND STIMULATION FOR FITTING COCHLEAR IMPLANTS

This application is a continuation of U.S. patent application Ser. No. 17/262,662, filed Jan. 22, 2021, which in turn is a 371 national phase entry of Patent Cooperation Treaty Application PCT/US2019/038875, filed Jun. 25, 2019, which in turn claims priority from U.S. Provisional Patent Application 62/702,944, filed Jul. 25, 2018. Each of the above-described applications is hereby incorporated herein by reference in their entireties.

TECHNICAL FIELD

The present invention relates to hearing implant systems, and more specifically, to custom fitting of hearing implant systems such as cochlear implants.

BACKGROUND ART

Figure 1:
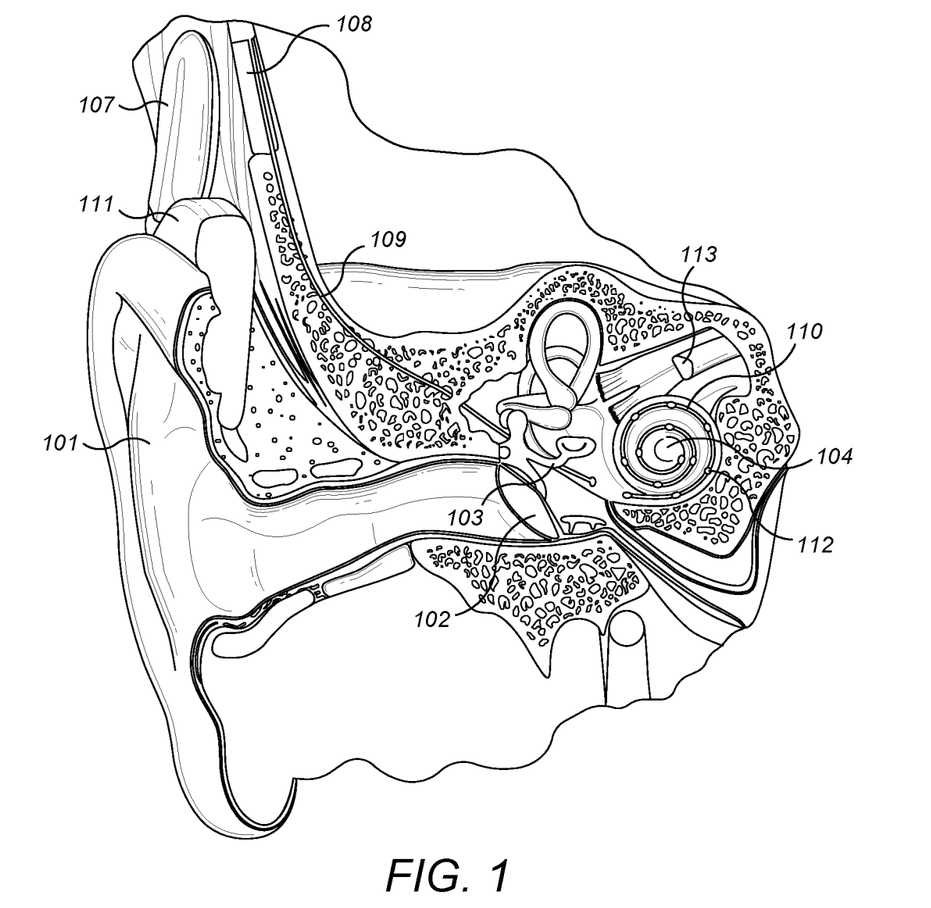
FIG. 1 shows anatomical structures of a typical human ear with a cochlear implant system.

A normal ear transmits sounds as shown in FIG. 1 through the outer ear 101 to the tympanic membrane (eardrum) 102, which vibrates the ossicles of the middle ear 103 (malleus, incus, and stapes). The stapes footplate is positioned in the oval window 106 that forms an interface to the fluid filled inner ear (the cochlea) 104. Movement of the stapes generates a pressure wave in the cochlea 104 that stimulates the sensory cells of the auditory system (hair cells). The cochlea 104 is a long narrow duct wound spirally around its central axis (called the modiolus) for approximately two and a half turns. The cochlea 104 includes an upper channel known as the scala vestibuli, a middle channel known as the scala media and a lower channel known as the scala tympani. The hair cells connect to the spiral ganglion cells of the cochlear nerve 105 that reside in the modiolus. In response to received sounds transmitted by the middle ear 103, the fluid-filled cochlea 104 functions as a transducer to generate electric pulses which are transmitted to the cochlear nerve 105, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid or middle ear implant may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system, including an external microphone that provides an audio signal input to an external signal processor 111 where various signal processing schemes can be implemented. The processed signal is then converted into a digital data format, such as a sequence of data frames, for transmission via external transmitting coil 107 into the implant receiver 108. Besides receiving the processed audio information, the implant receiver 108 also performs additional signal processing such as error correction, pulse formation, etc., and produces a stimulation pattern (based on the extracted audio information) that is sent through an electrode lead 109 to an implanted electrode array 110. The electrode array 110 includes multiple electrode contacts 112 (also referred to as electrode channels) on its surface that provide selective stimulation of the cochlea 104.

Figure 2:
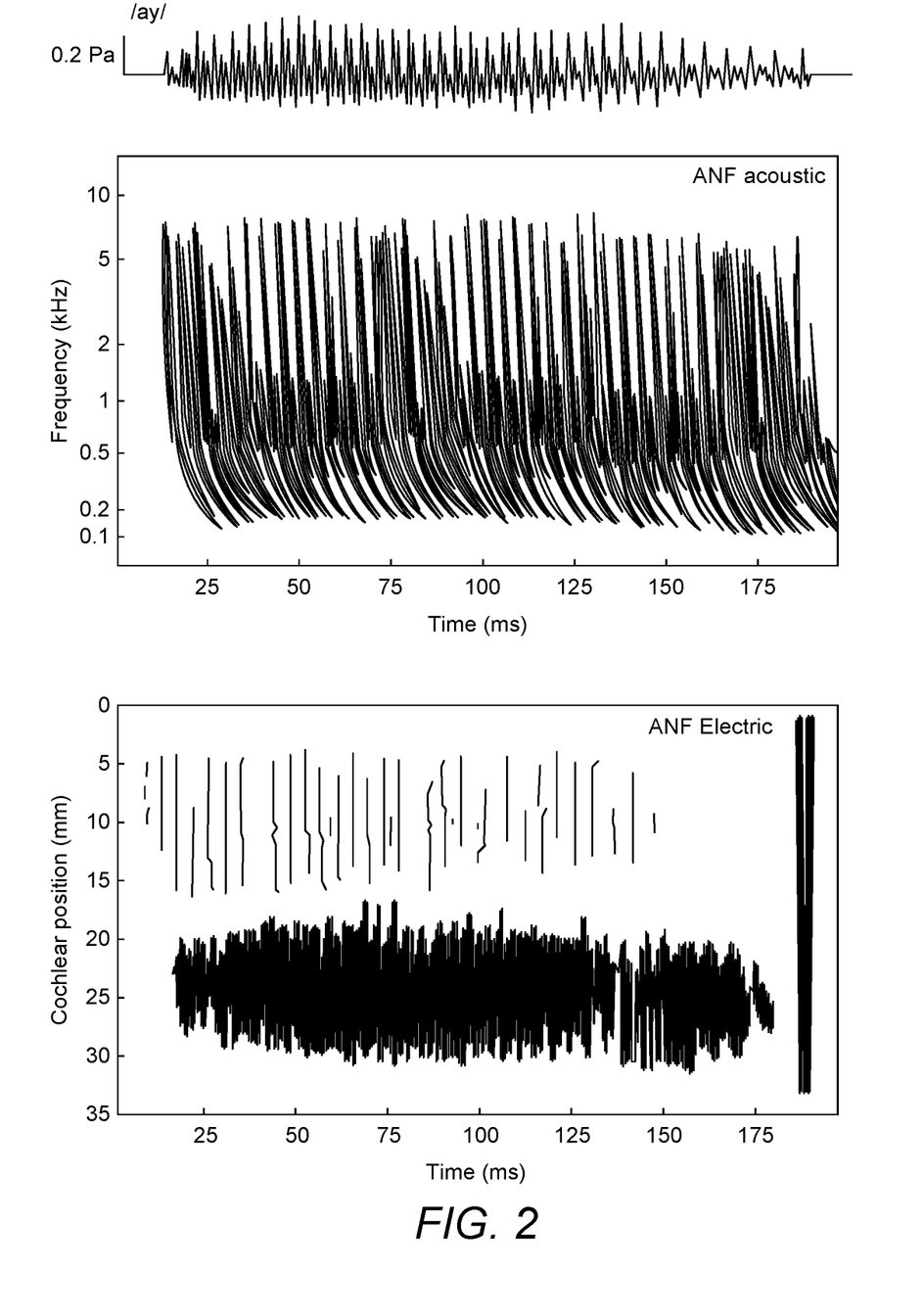
FIG. 2 shows an example of signal processing using the cochlear implant stimulation (CIS) stimulation strategy

A relatively small number of electrode channels are each associated with relatively broad frequency bands, with each electrode contact addressing a group of neurons with an electric stimulation pulse having a charge that is derived from the instantaneous amplitude of the signal envelope within that frequency band. Current cochlear implant coding strategies map the different sound frequency channels onto different locations within the cochlea. FIG. 2 shows one example of the processing of a signal using the cochlear implant stimulation (CIS) stimulation strategy. The top of FIG. 2 shows the sound pressure characteristics of a spoken "A" (/ay/) at a sound level of 67.2 dB. The middle waveform in FIG. 2 shows a normal healthy auditory system response. The bottom waveform in FIG. 2 shows a neural response of the auditory nerve fibers under CIS stimulation.

Figure 3:
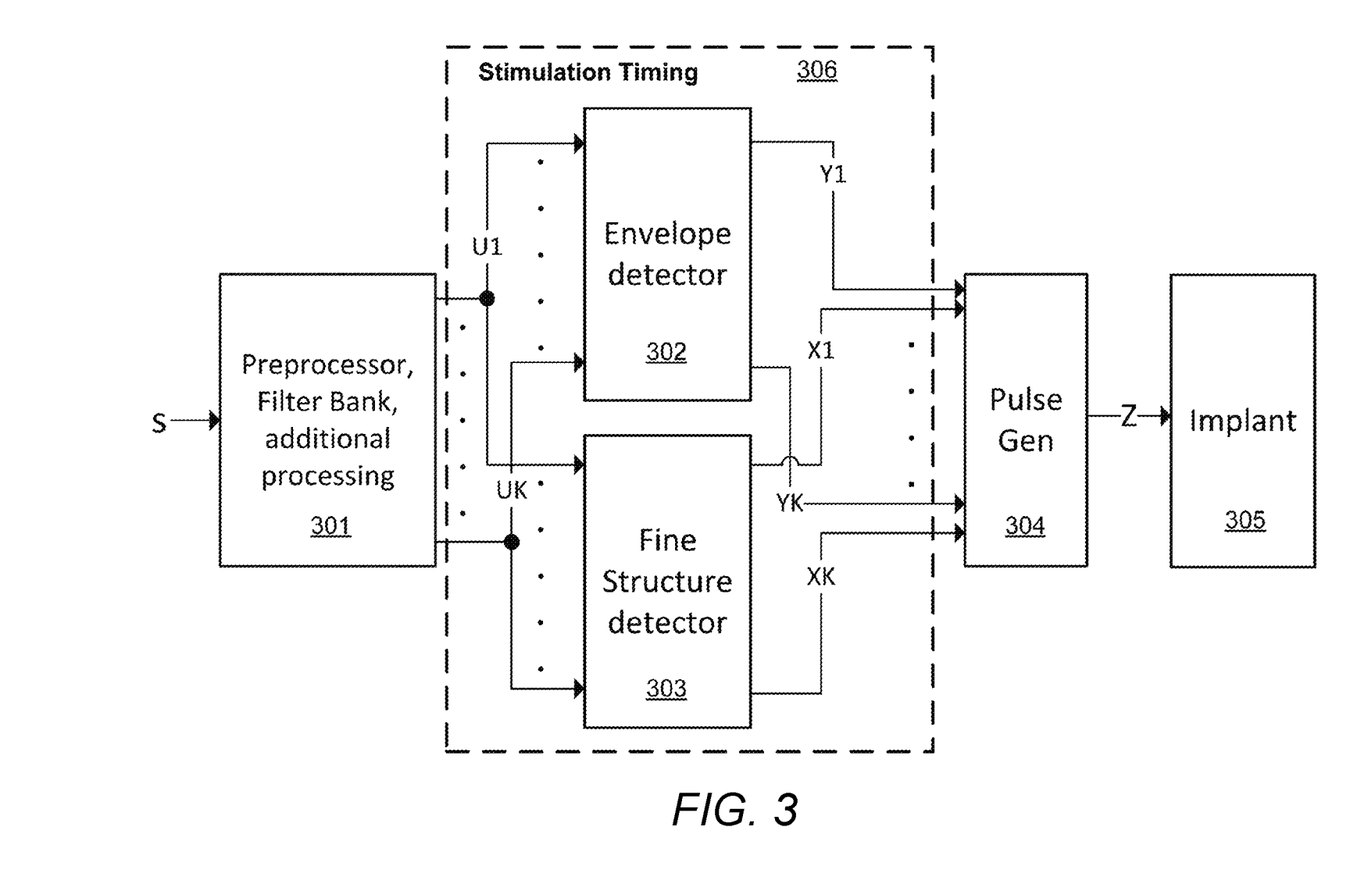
FIG. 3 shows various functional blocks in a signal processing arrangement for a typical cochlear implant system

FIG. 3 shows various functional blocks in a signal processing arrangement for producing electrode stimulation signals to electrode contacts in an implanted cochlear implant array according to a typical hearing implant system. A pseudo code example of such an arrangement can be set forth as:
Input Signal Preprocessing:
  BandPassFilter (input_sound, band_pass_signals)
Envelope Extraction:
  BandPassEnvelope (band_pass_signals, band_pass_envelopes)
Stimulation Timing Generation:
  TimingGenerate (band_pass_signals, stim timing)
Pulse Generation:
  PulseGenerate (band_pass_envelopes, stim timing, out_pulses)
The details of such an arrangement are set forth in the following discussion.

In the signal processing arrangement shown in FIG. 3, the initial input sound signal is produced by one or more sensing microphones, which may be omnidirectional and/or directional. Preprocessor Filter Bank 301 pre-processes this input sound signal with a bank of multiple parallel band pass filters (e.g. Infinite Impulse Response (IIR) or Finite Impulse Response (FIR)), each of which is associated with a specific band of audio frequencies, for example, using a filter bank with 12 digital Butterworth band pass filters of 6th order, Infinite Impulse Response (IIR) type, so that the acoustic audio signal is filtered into some K band pass signals, $U_1$ to $U_K$ where each signal corresponds to the band of frequencies for one of the band pass filters. Each output of sufficiently narrow CIS band pass filters for a voiced speech input signal may roughly be regarded as a sinusoid at the center frequency of the band pass filter which is modulated by the envelope signal. This is also due to the quality factor ($Q \approx 3$) of the filters. In case of a voiced speech segment, this envelope is approximately periodic, and the repetition rate is equal to the pitch frequency. Alternatively and without limitation, the Preprocessor Filter Bank 301 may be implemented based on use of a fast Fourier transform (FFT) or a short-time Fourier transform (STFT). Based on the tonotopic organization of the cochlea, each electrode contact in the scala tympani typically is associated with a specific band pass filter of the Preprocessor Filter Bank 301. The Preprocessor Filter Bank 301 also may perform other initial signal processing functions such as and without limitation automatic gain control (AGC) and/or noise reduction and/or wind noise reduction and/or beamforming and other well-known signal enhancement functions. An example of pseudocode for an infinite impulse response (IIR) filter bank based on a direct form II transposed structure is given by Fontaine et al., Brian Hears: Online Auditory Processing Using Vectorization Over Channels, Frontiers in Neuroinformatics, 3011; incorporated herein by reference in its entirety.

The band pass signals $U_1$ to $U_K$ (which can also be thought of as electrode channels) are output to a Stimulation Timer 306 that includes an Envelope Detector 302 and Fine Structure Detector 303. The Envelope Detector 302 extracts characteristic envelope signals outputs $Y_1, \ldots, Y_K$ that represent the channel-specific band pass envelopes. The envelope extraction can be represented by $Y_k=LP(|U_k|)$, where $|\cdot|$ denotes the absolute value and $LP(\cdot)$ is a low-pass filter; for example, using 12 rectifiers and 12 digital Butterworth low pass filters of 2nd order, IIR-type. Alternatively, the Envelope Detector 302 may extract the Hilbert envelope, if the band pass signals $U_1, \ldots, U_K$ are generated by orthogonal filters.

The Fine Structure Detector 303 functions to obtain smooth and robust estimates of the instantaneous frequencies in the signal channels, processing selected temporal fine structure features of the band pass signals $U_1, \ldots, U_K$ to generate stimulation timing signals $X_1, \ldots, X_K$. The band pass signals $U_1, \ldots, U_K$ can be assumed to be real valued signals, so in the specific case of an analytic orthogonal filter bank, the Fine Structure Detector 303 considers only the real valued part of $U_k$. The Fine Structure Detector 303 is formed of K independent, equally-structured parallel sub-modules.

The extracted band-pass signal envelopes $Y_1, \ldots, Y_K$ from the Envelope Detector 302, and the stimulation timing signals $X_1, \ldots, X_K$ from the Fine Structure Detector 303 are output from the Stimulation Timer 306 to a Pulse Generator 304 that produces the electrode stimulation signals Z for the electrode contacts in the implanted electrode array 305. The Pulse Generator 304 applies a patient-specific mapping function—for example, using instantaneous nonlinear compression of the envelope signal (map law)—That is adapted to the needs of the individual cochlear implant user during fitting of the implant in order to achieve natural loudness growth. The Pulse Generator 304 may apply logarithmic function with a form-factor C as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals. The electrode stimulation signals typically are a set of symmetrical biphasic current pulses.

For an audio prosthesis such as a cochlear implant to work correctly, some patient-specific operating parameters need to be determined in a fit adjustment procedure where the type and number of operating parameters are device dependent and stimulation strategy dependent. Possible patient-specific operating parameters for a cochlear implant include:

$THR_1$ (lower detection threshold of stimulation amplitude) for Electrode 1
$MCL_1$ (most comfortable loudness) for Electrode 1
Phase Duration for Electrode 1
$THR_2$ for Electrode 2
$MCL_2$ for Electrode 2
Phase Duration for Electrode 2
. . . .
Pulse Rate
Number of fine structure channels
Compression
Parameters of frequency→electrode mapping
Parameters describing the electrical field distribution These patient-specific operating parameters are saved in a file referred to as a fit map. A given system may have multiple patient-specific fit maps for different listening environments; for example, there may be one fit map for a quiet environment and a different fit map for a noisy environment. The better the fit map, the more closely the hearing experience from the electrical stimulation signals resembles the natural acoustic hearing experience of unimpaired individuals.

One common method for fit adjustment is to behaviorally find the threshold (THR) and most comfortable loudness (MCL) value for each separate electrode contact. See for example, Rätz, *Fitting Guide for First Fitting with MAESTRO 2.0*, MED-EL, Fürstenweg 77a, 6020 Innsbruck, 1.0 Edition, 2007. AW 5420 Rev. 1.0 (English_EU); incorporated herein by reference. Other alternatives/extensions are sometimes used with a reduced set of operating parameters; e.g. as suggested by Smoorenburg, Cochlear Implant Ear Marks, University Medical Centre Utrecht, 2006; and U.S. Patent Application 20060235332; which are incorporated herein by reference. Typically each stimulation channel is fitted separately without using the information from already fitted channels. The stimulation current on a given electrode typically is increased in steps from zero until the MCL or THR is reached.

One approach for an objective measurement of MCLs and THRs is based on the measurement of the ECAPs (Electrically Evoked Compound Action Potentials), as described by Gantz et al., *Intraoperative Measures of Electrically Evoked Auditory Nerve Compound Action Potentials*, American Journal of Otology 15 (2):137-144 (1994), which is incorporated herein by reference. In this approach, a recording electrode in the scala tympani of the inner ear is used. The overall response of the auditory nerve to an electrical stimulus is measured very close to the position of the nerve excitation. This neural response is caused by the superposition of single neural responses at the outside of the axon membranes. The amplitude of the ECAP at the measurement position is typically in the ranges of µV. When performing objective measurements such as ECAP measurements in existing cochlear implant systems, usually each electrode contact of the implantable electrode array is scanned separately, increasing the stimulation signal current on an electrode contact in steps from zero or a very low level until an ECAP response is detected. Other objective measurement approaches are also known, such as electrically evoked stapedius reflex thresholds (eSRT).

Once the fit parameters such as MCL and THR are initially established based on objective measurements, then an audiologist can further fine tune the fit map based on their experience and any available subjective feedback from the individual patient to modify the existing fit map by scaling, tilting, smoothing, or changing the shape of the fit map. However, the fitting audiologist needs to have many years of clinical experience and the fitting process can be quite time consuming. It is not trivial to test even some of the many possible adjustment combinations. In addition, patient feedback is not always available; for example, when the patient is a small child.

Several attempts have been made to make fitting faster or more automatic. The most recent development within this field is Med-El's MAESTRO 7.0.1 Auditory Response Telemetry based fitting entitled "ARTFit" which targets fitting based on objective measures. During these objective measures the volume is increased from low to high until an objective response is measured. Ideally, this process is performed on every electrode until a response is found or until the subject feels the need to indicate that the stimulation has become too uncomfortable. In essence this means that although an objective response is measured the subject still needs to be able to indicate that the stimulation has become too loud in order to obtain that objective response.

Despite the fact that the measurements can be performed with a sedated patient or a patient under general anesthesia, it is still uncommon to routinely perform objective measurements during implantation surgery due to time constraints. Current fitting strategies require adjustment of individual channels and then adjustments of overall loudness. The process needs to be finished completely in order to get a reliable map. Some efforts have been made to replace parts of the process with objective measurements. These require relatively lengthy measurements which by themselves require loudness judgments to function. Once the objective measurements are completed they lead to a MAP profile which then again needs to be live adjusted.

SUMMARY

Embodiments of the present invention are directed to fitting arrangements for fitting electrode contacts of cochlear implant electrode array implanted in a cochlea of an implanted patient. This involves iteratively fitting multiple fitting electrode contacts by for each of the fitting electrode contacts: i. delivering fitting stimulation signals to the fitting electrode contact and at least one neighboring electrode contact to stimulate adjacent auditory neural tissue, wherein the fitting stimulation signals are characterized by a charge level distribution function having a non-zero noise level charge at the at least one neighboring electrode contact and a response level charge much greater than the noise level charge at the fitting electrode contact, and ii. obtaining patient responses from the implanted patient to the fitting stimulation signals. A patient-specific fit map is then defined for the electrode contacts of cochlear implant electrode array based on the patient responses.

In further specific embodiments, the charge level distribution function may be a Gaussian or geometric distribution function with a peak corresponding to the response level charge. The fitting electrode contacts may be fit sequentially starting from an apical end of the electrode array back along the length of the electrode array. Or the fitting electrode contacts may be fit in a non-linear order along the electrode array and/or in an alternating sequence of every other electrode contact along the length of the electrode array. The patient responses may include subjective and/or objective response measurements.

Embodiments of the present invention also include a cochlear implant system fit to an implanted patient using any of the above methods.

DETAILED DESCRIPTION

Embodiments of the present invention are directed to cochlear implant fitting arrangements that produce a patient-specific fit map more quickly than with existing approaches without undesirably elevating the risk of overstimulation (without exceeding MCL). The described method applies stimulation to the cochlear implant user in a most comfortable way by masking neighboring electrodes. This method also applies the charge levels on more than one electrode contact to provide a more time efficient fitting procedure.

Figure 4:
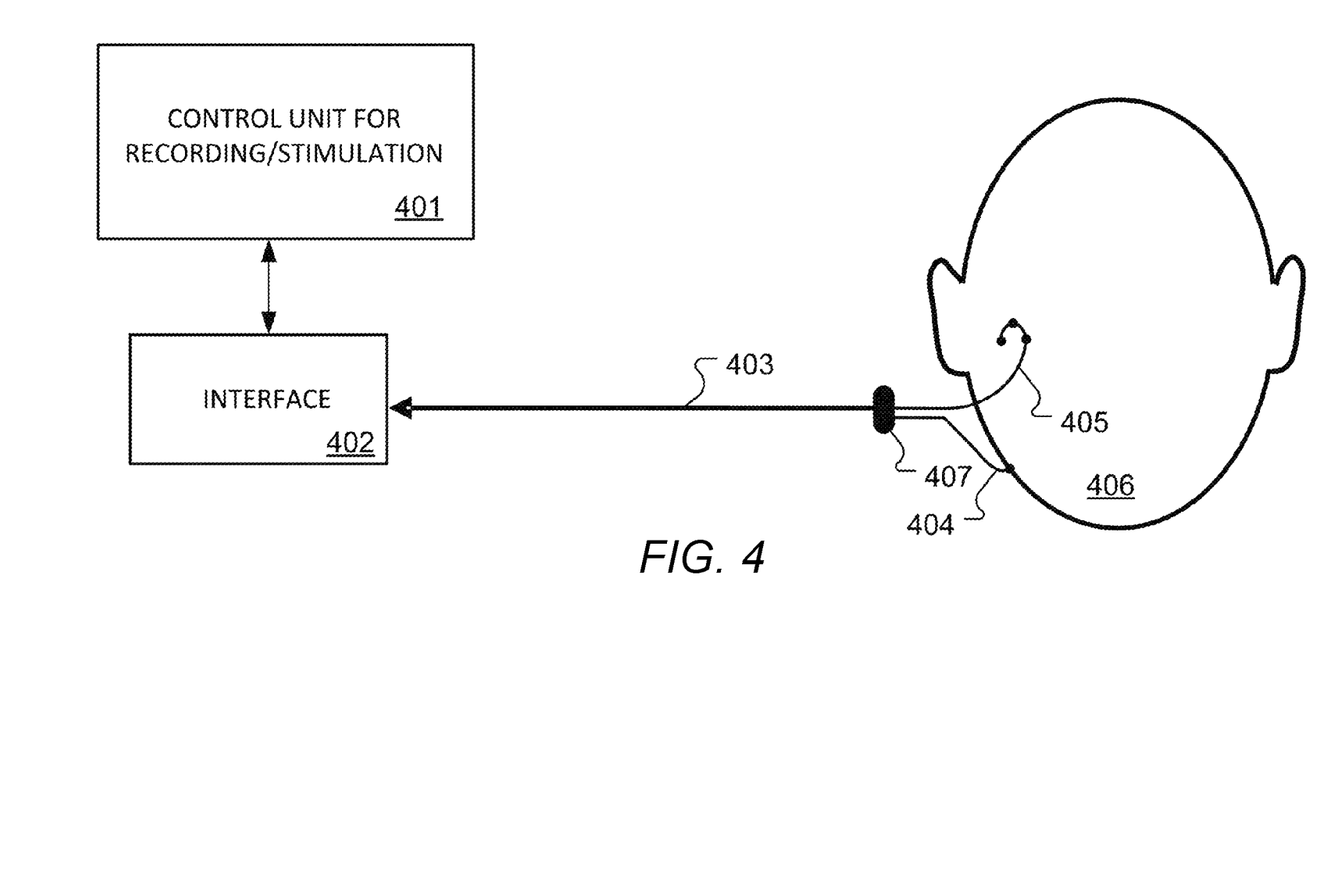
FIG. 4 shows a block diagram of a cochlear implant fitting system according to an embodiment of the present invention.

FIG. 4 shows a block diagram of a cochlear implant fitting system according to an embodiment of the present invention. Control Unit 401 for Recording and Stimulation, for example, a Med-El Maestro Cochlear Implant (CI) system, generates stimulation signals and analyzes response measurements. Connected to the Control Unit 401 is an Interface Box 402, for example, a Diagnostic Interface System such as the DIB II conventionally used with the Maestro CI system that formats and distributes the input and output signals between the Control Unit 401 and the system components implanted in the Patient 406. For example, as shown in FIG. 4, there may be an Interface Lead 403 connected at one end to the Interface Box 402 and at the other end having Electrode Plug 407 that then divides into a Cochlear Implant Electrode Array 405 and an Extra-Cochlear Ground Electrode 404. The Control Unit 401 is configured for fitting electrode contacts of the Cochlear Implant Electrode Array 405. The Control Unit 401 includes a fitting processor with at least one hardware implanted processor device and is controlled by software instructions to perform the fitting process including delivering to at least one of the electrode contacts a test stimulation sequence which is at a variable charge level and a variable stimulation rate over time. After delivering a stimulation pulse, an electrode contact on the Cochlear Implant Electrode Array 405 may be used as a sensing element to determine current and voltage characteristics of the adjacent tissue.

Figure 5:
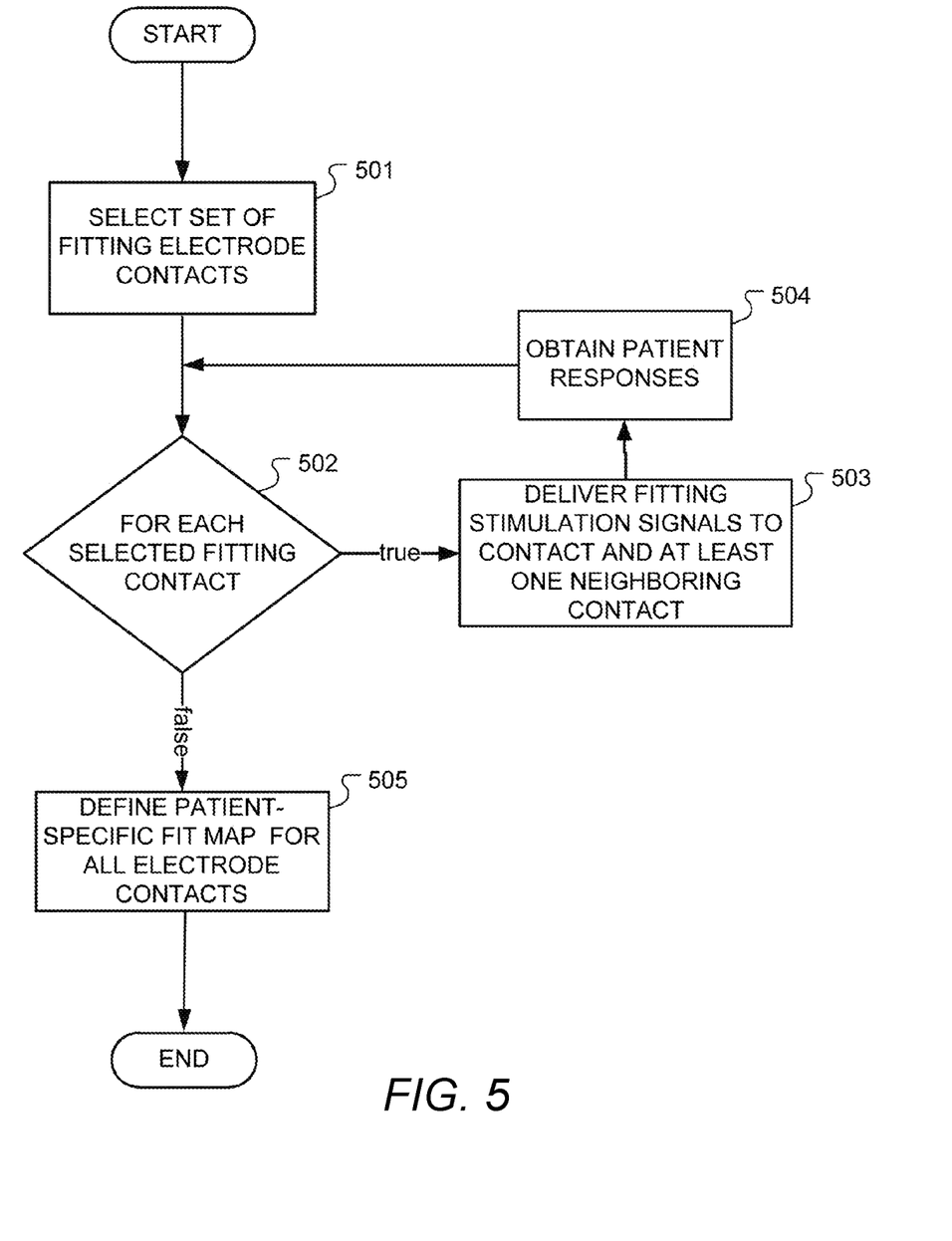
FIG. 5 shows various logical steps in a fitting process according to an embodiment of the present invention.

More specifically, the fitting system depicted in FIG. 4 is operated to iteratively fit multiple fitting electrode contacts on the implanted electrode array following the basic logical steps as shown in FIG. 5. First, step 501, a set of fitting contacts is selected. For example, this may be all of the electrode contacts sequentially starting from an apical end of the electrode array back along the length of the electrode array. Or the set of selected fitting electrode contacts may be all of the electrode contacts fit in a non-linear order along the electrode array. Or the set of the elected fitting contacts may be an alternating sequence of every other electrode contact along the length of the electrode array. The latter case reduces the required time by 50%. Fitting parameters for the unselected electrode contacts may be calculated by interpolating (or extrapolating) from the parameters derived for the selected electrode contacts.

Then, for each of the fitting electrode contacts, step 502, fitting stimulation signals are delivered to the fitting electrode contact and at least one neighboring electrode contact to stimulate adjacent auditory neural tissue, step 503. The fitting stimulation signals are characterized by a charge level distribution function that has a non-zero noise level charge at the at least one neighboring electrode contact and a response level charge much greater than the noise level charge at the fitting electrode contact. For a distribution function with a peak k and parameter p, and a noise function with random values from 0 to q:

$$char,geLvl(x,n)=chargeLvl(x,n-1)+dist(k,p)+noise(x,q)$$

$$chargeLvl(x,0)=constant$$

$$noise(k,q)=0.$$

Patient responses, which may include subjective and/or objective response measurements, are then obtained from the implanted patient to the fitting stimulation signals, step 504. This is done for each fitting electrode contact while saving the charge level of each individual electrode contact that provides the stimulation signals. A patient-specific fit map is defined for the electrode contacts of cochlear implant electrode array based on the patient responses, step 505.

Figure 6A:
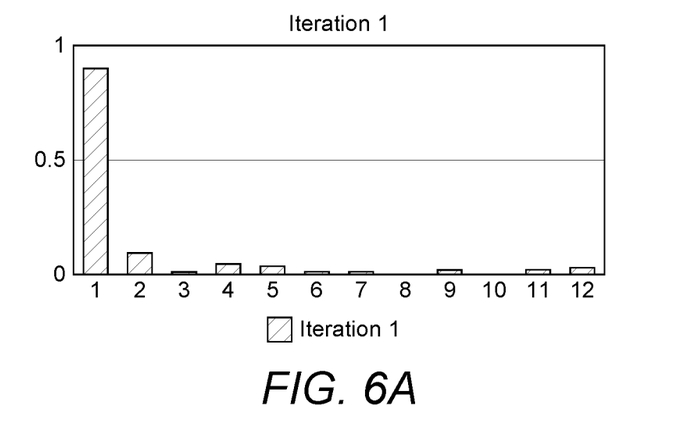
FIGS. 6A-6C show charge distributions for a fitting process according to one specific embodiment.
Figure 6B:
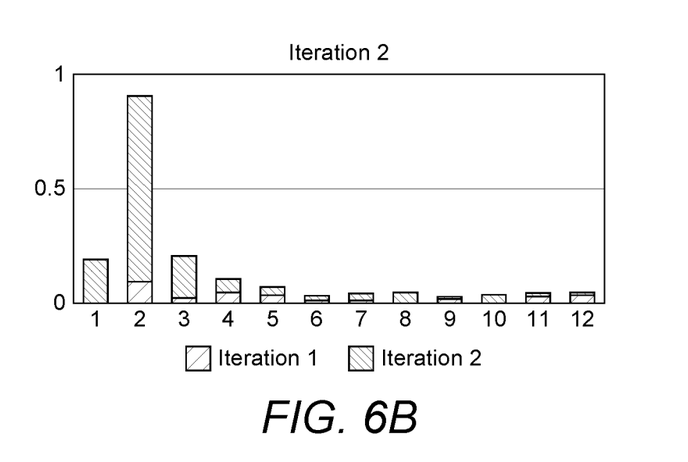
Figure 6C:
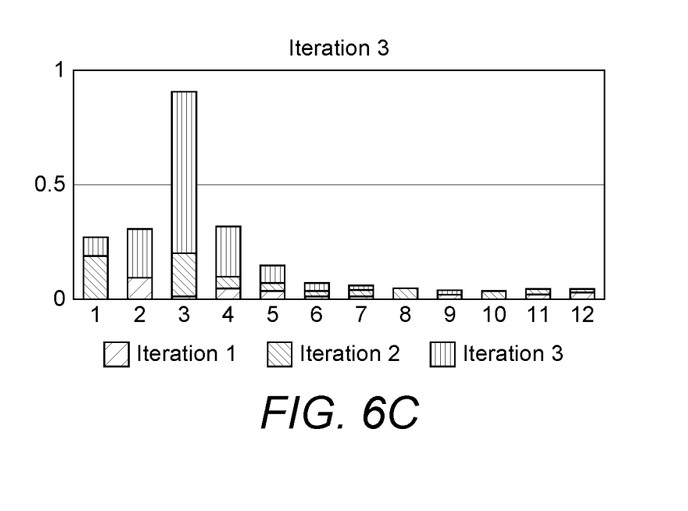
Figure 7A:
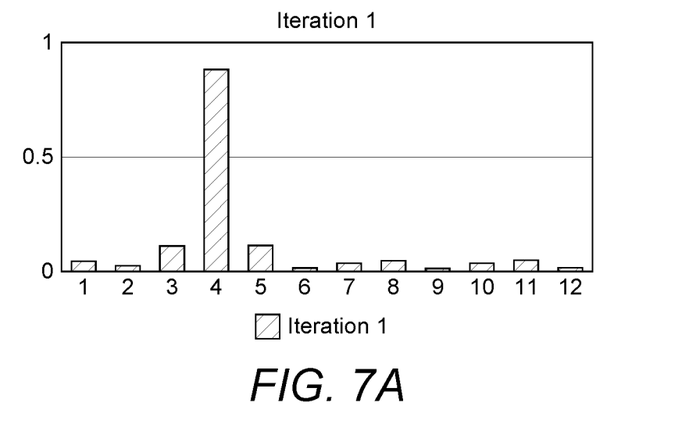
FIGS. 7A-7C show charge distributions for a fitting process according to another specific embodiment.
Figure 7B:
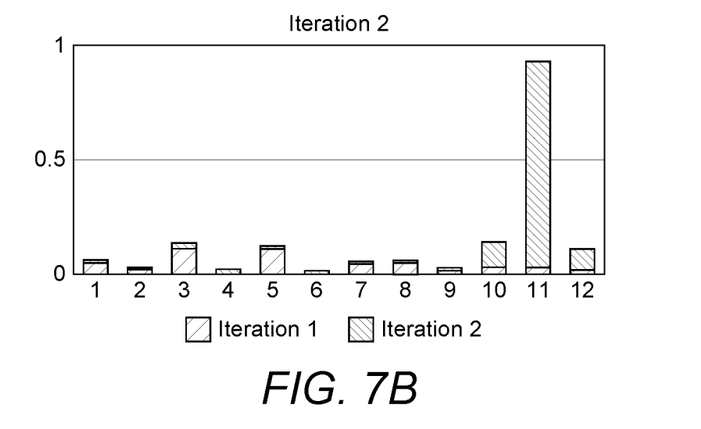
Figure 7C:
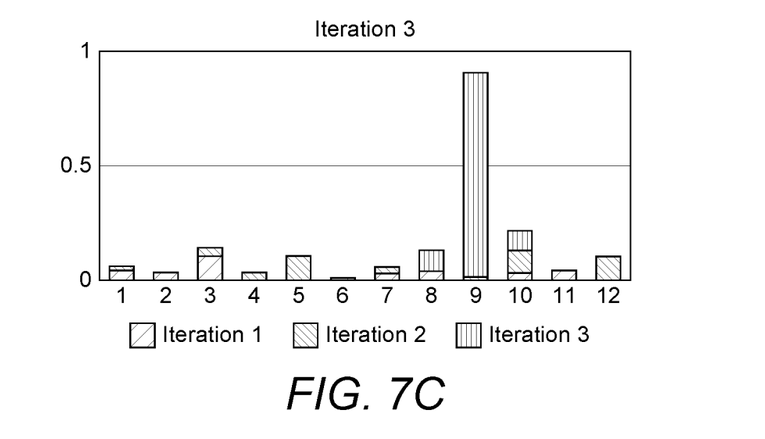

FIGS. 6A-6C show charge distributions for three iterations of a fitting process where the charge level distribution function is a Gaussian distribution function with a peak corresponding to the response level charge. For example, one specific Gaussian distribution function may have a standard derivative $\sigma=0.5$ and $\mu=1$. FIGS. 7A-7C show charge distributions for three iterations of a fitting process where the charge level distribution function is a geometric distribution function with a peak corresponding to the response level charge with $p=0.9$, $p\in(0,1)$ and $k=1$, where the values of y and k represent the electrode contact currently being fitted.

These techniques are especially useful for an electrode array with a low number of electrode contacts since the number of iterations needed equals the number of electrode contacts. It will be appreciated that the charge level on all electrode contacts steadily rises with the number of iterations. This means that the initial charge level for the response measurement is higher, but still the desired maximum charge level can be calculated more quickly, as charge levels should not get too high. Alternatively a relative factor between the selected fitting electrode contact and the at least one neighboring electrode contact can be chosen to avoid the at least one neighboring electrode contact being too loud. Alternatively this risk can be avoided by setting a maximum charge level limit over all the electrode contacts which cannot be surpassed by the charge levels on neighboring electrode contacts.

The fitting process typically may start with a flat map at MCL levels. A clinical randomization factor may be selectable depending on the ability of the patient to judge loudness. The patient then can be presented with different versions of the randomized map with instructions to judge if a map is "too loud". Each of the maps can be presented for 5 seconds unless the user presses a "too loud"/"skip" button. The longer the fitting process runs, the better the final map will be, and the final map is based on the maximum charge level measured for each electrode contact.

Background stimulation on the neighboring electrode contacts makes the patient more loudness tolerant, particularly as to electrode contacts near the electrode opening into the cochlea where high frequency sounds are perceived. A higher starting value is chosen for each consecutive electrode contact based on the previous iteration of stimulation, which leads to a more time efficient fitting procedure. There also is better mimicking of channel interaction during the fitting of each individual electrode contact so the channel interaction portion of the fitting process can be omitted.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A non-transitory tangible computer-readable medium having instructions thereon for fitting an implanted patient and a hearing implant system having an implanted electrode array with a plurality of electrode contacts, the instructions comprising:
   iteratively fitting a plurality of fitting electrode contacts by, for each of the fitting electrode contacts:
   i. delivering fitting stimulation signals to the fitting electrode contact and at least one neighboring electrode contact to stimulate adjacent auditory neural tissue, wherein the fitting stimulation signals are characterized by a charge level distribution function having a non-zero noise level charge at the at least one neighboring electrode contact and a response level charge much greater than the noise level charge at the fitting electrode contact, and
   ii. obtaining patient responses from the implanted patient to the fitting stimulation signals; and defining a patient-specific fit map for the electrode contacts of cochlear implant electrode array based on the patient responses.

2. The computer-readable medium according to claim 1, wherein the charge level distribution function is a Gaussian distribution function with a peak corresponding to the response level charge.

3. The computer-readable medium according to claim 1, wherein the charge level distribution function is a geometric distribution function with a peak corresponding to the response level charge.

4. The computer-readable medium according to claim 1, wherein the fitting electrode contacts are fit sequentially starting from an apical end of the electrode array back along the length of the electrode array.

5. The computer-readable medium according to claim 1, wherein the fitting electrode contacts are fit in a non-linear order along the electrode array.

6. The computer-readable medium according to claim 1, wherein the fitting electrode contacts are fit in an alternating sequence of every other electrode contact along the length of the electrode array.

7. The computer-readable medium according to claim 1, wherein the patient responses include subjective response measurements.

8. The computer-readable medium according to claim 1, wherein the patient responses include objective response measurements.

* * * * *